United States Patent
Tuchman et al.

(10) Patent No.: US 8,284,404 B2
(45) Date of Patent: Oct. 9, 2012

(54) CAVITY ENHANCED TRACE GAS DETECTION GRADIOMETER

(75) Inventors: Ari K. Tuchman, Palo Alto, CA (US); John K. Stockton, Redwood City, CA (US)

(73) Assignee: Entanglement Technologies, Inc., Burlingame, CA (US)

( * ) Notice: Subject to any disclaimer, the term of this patent is extended or adjusted under 35 U.S.C. 154(b) by 0 days.

(21) Appl. No.: 13/187,747

(22) Filed: Jul. 21, 2011

(65) Prior Publication Data
US 2011/0273713 A1 Nov. 10, 2011

Related U.S. Application Data

(63) Continuation of application No. 12/246,659, filed on Oct. 7, 2008, now Pat. No. 8,040,518.

(51) Int. Cl.
*G01N 21/00* (2006.01)
(52) U.S. Cl. ......... 356/438; 356/432; 356/439; 356/440
(58) Field of Classification Search .......... 356/432–439, 356/440
See application file for complete search history.

(56) References Cited

U.S. PATENT DOCUMENTS

| 5,528,040 | A | 6/1996 | Lehmann |
| 6,094,267 | A | 7/2000 | Levenson et al. |
| 6,781,696 | B1 | 8/2004 | Rosenberger et al. |
| 6,927,858 | B2 * | 8/2005 | Boone et al. ......... 356/437 |
| 7,113,286 | B2 | 9/2006 | Yan |
| 7,570,360 | B1 * | 8/2009 | Tkachuk ............. 356/437 |
| 7,586,114 | B2 * | 9/2009 | Cole et al. ........... 250/575 |
| 2004/0001204 | A1 * | 1/2004 | Boone et al. ......... 356/437 |
| 2006/0192967 | A1 | 8/2006 | Kluczynski |

* cited by examiner

*Primary Examiner* — Tarifur Chowdhury
*Assistant Examiner* — Isiaka Akanbi
(74) *Attorney, Agent, or Firm* — Rankin, Hill & Clark LLP

(57) ABSTRACT

A method and device for measuring trace levels of particles in an air sample is described. A device operating in a gradiometer configuration with two cavities built from a monolithic structure and utilizing a single probe laser, provides common mode subtraction of acoustic, vibrational, laser intensity and other noise sources, which allows sensitivity more closely approaching the quantum limit. Differential measurements between the two cavities occur simultaneously, which reduces errors due to cavity drift. Absorptive gradiometry can therefore provide noise immune detection for trace gasses, including broad linewidth absorbers where frequency-noise immune schemes are not practical. Differential measurements can be used for background subtraction, sensing vapor plum gradients and determining vapor plume propagation direction.

18 Claims, 3 Drawing Sheets

CAVITY ENHANCED TRACE GAS DETECTION GRADIOMETER

TECHNICAL FIELD

This invention relates generally to the detection of trace gases.

BACKGROUND

Trace gas detection has applications ranging from explosive and chemical weapons detection to semiconductor manufacturing and medical diagnostics, which utilize a large range of platform technologies. For many applications such as explosive vapor plume detection, extreme sensitivity is required due to the low concentrations and small cross sections of common explosives. Concentrations can be below 1 part per billion (ppb) and a typical optical cross section for TNT is less than $10^{-17}$ cm$^2$ (and can be several orders of magnitude smaller, depending on the wavelength).

Absorption measurements represent one leading technique for trace gas detection. Small changes in the transmitted intensity of a probe laser beam are used to determine the presence of absorbing particles. In the photon shot noise detection limit, the single pass sensitivity is $$\alpha_{sn} = \left(\frac{2eB}{\eta P}\right)^{1/2} \frac{1}{L}$$

where the $\alpha_{sn}$ is the minimum measurable absorption, B is the measurement bandwidth, $\eta$ is the detector responsivity (A/W), e is the electron charge, and P is the power incident on the detector and L is the interaction length. For 1 mW of incident light and 1 second measurement times, absorption sensitivities approaching $10^{-9}$/cm are in principle attainable. Precise stabilization of the laser intensity is generally seen as required for this technique. In practice, a much worse sensitivity is usually achieved.

The sensitivity of absorption detection of trace gases can be enhanced by placing the absorbing sample in a high finesse optical cavity which allows multi-pass interaction between the probe beam and the sample. The light can interact with a particle each time it reflects off the cavity mirrors, which can be greater than $10^5$ times (corresponding to cavity finesse, F~$10^5$), as can be achieved with state of the art mirror technology in certain wavelength ranges. This provides a signal amplification approximately equal to the finesse, so that one obtains a shot noise limited minimum sensitivity of $$\alpha_{sn} = \left(\frac{2eB}{\eta P}\right)^{1/2} \frac{\pi}{2FL}.$$

A high finesse cavity is also a narrow frequency discriminator which only allows the transmission of a narrow range of frequencies. Therefore any frequency fluctuations in the probe laser are mapped onto amplitude fluctuations in the light transmitted through the cavity, which can further exacerbate the technical problem of intensity stabilization. One approach to circumventing this problem is to measure the decay curve of the intensity transmitted through the cavity when the light is extinguished. The light intensity can be fit to an exponential decay function, whose time constant $\tau$ (the cavity ring down time) is related to the cavity loss which includes absorption through the cavity, as discussed in K. Lehmann, U.S. Pat. No. 5,528,040. For a two-mirror cavity $$\frac{1}{c\tau} = \alpha + \frac{2(1-R)+A}{2L}$$

where c is the speed of light, R is the mirror reflectivity, and A denotes the loss due to scatter and absorption in the mirrors. The measured ring down time of the cavity containing the absorber is then compared to the empty cavity ring down time $\tau_{empty}$ to extract the additional absorption due to a trace element $$\frac{1}{\tau} - \frac{1}{\tau_{empty}} = c\alpha.$$

This measurement is, by design, independent of any light intensity fluctuations. The background trace is often taken in close temporal proximity to the signal trace, however since they are nevertheless separated in time, additional noise can be introduced in the measurement, due, for example, to slight changes in the cavity properties as well as other technical noise sources.

For narrow linewidth absorbers, multiple frequency laser beams can be transmitted simultaneously through the cavity separated in frequency by an integer multiple of the free spectral range (FSR=c/2 L). If one of the laser beams is resonant with the trace absorber and additional beams are far-off resonant, then the measured relative phase shift between the beams can be used to determine the absorber concentration (Ye 1998). Since the multiple-frequency measurements utilize a common cavity, and the frequency sidebands can be derived from a single laser source, much of the noise is common mode and cancels, and therefore this technique is often referred to as noise-immune. It has succeeded in measuring absorption sensitivities in molecular overtones approaching the photon shot nose limit.

For broadband absorbers, it is often not feasible to discriminate between comparable absorption levels at separated wavelengths, where both wavelengths are derived from the same master laser. Thus, one cannot implement conventional noise-immune frequency discriminating techniques with one frequency sideband far off-resonant from the absorber and one on resonance. Explosives represent such absorbers where, for example, the linewidth of a TNT resonance in the mid-IR region (7 microns) is ~0.1 microns.

There is thus a need for trace gas detectors with improved sensitivity and ability to handle broadband absorbers.

SUMMARY OF THE INVENTION

A trace gas detector is provided comprising two or more high finesse optical cavities constructed from a monolithic structure, a laser beam common to both cavities which frequency stabilizes the cavity lengths, a reference atomic vapor cell as a frequency reference, a controller which controls the light intensity and frequencies and receives information detected by two or more photodetectors which monitor the light transmitted through the cavities in order to extract the relative absorption between the cavities which can be used to determine the gradient concentration of an absorbing vapor, a sampling mechanism which samples air from the environment and can sample from a range of locations as controlled by the controller. In another embodiment an array of cavities is used to identify components of a gas mixture by extracting populations of component gases based on differing diffusion coefficients.

DETAILED DESCRIPTION OF THE INVENTION

Definitions and Overview

It is to be understood that, unless otherwise indicated, this invention is not limited to specific atoms or molecules or specific arrangements of optical or electronic equipment or specific working materials. It is also to be understood that the terminology used herein is for the purpose of describing particular embodiments only, and is not intended to be limiting.

In describing and claiming the present invention, the following terminology will be used in accordance with the definitions set out below.

The singular forms "a," "an," and "the" include plural referents unless the context clearly dictates otherwise. Thus, for example, reference to "a laser" includes not only a single laser but also two or more lasers that may or may not be combined in a single composition, reference to "a mirror" includes a single mirrors well as two or more mirrors, and the like.

In this application, the term "cavity" is commonly used to denote an optical cavity.

In an aspect of the invention, a trace gas detection gradiometer with cavity enhanced sensitivity is described.

In general, two similar cavities are constructed in a monolithic passively stable device, with minimal, but common mode, thermal expansion. Probe lasers for the two cavities are derived from a single laser, using the same radiofrequency (RF) modulation source. Simultaneous absorptive measurements are made in both cavities. Low bandwidth, acoustic or thermal noise can be made common to both cavities by constructing the cavities from a single, monolithic block.

The second cavity can be used to measure trace gas concentration, simultaneously, but from gas sampled at a location separated from the first cavity sample. This gradiometer configuration allows relative absorption measurements between the two cavities where common mode noise, including contributions from common mode absorbers such as ambient atmosphere, can be subtracted from the measurement. Thus, the presence of environmentally homogeneous absorbers, such as water vapor, may have a reduced effect on the noise in the measurement. For detection of explosive vapor plumes above land mines with small footprints, for example, a gradiometer provides a significant advantage in locating the device as it is sensitive to small spatial gradients in explosive vapor concentration but may be less sensitive to common atmospheric absorber concentrations. This gradiometer can also be used in an embodiment with different sampling filters controlling the vapor input into each cavity, in order to measure relative concentrations of different contaminants. In addition the second cavity can be used as a background reference for measurements of trace gasses, where a sample is only introduced into one cavity.

Figure 1:
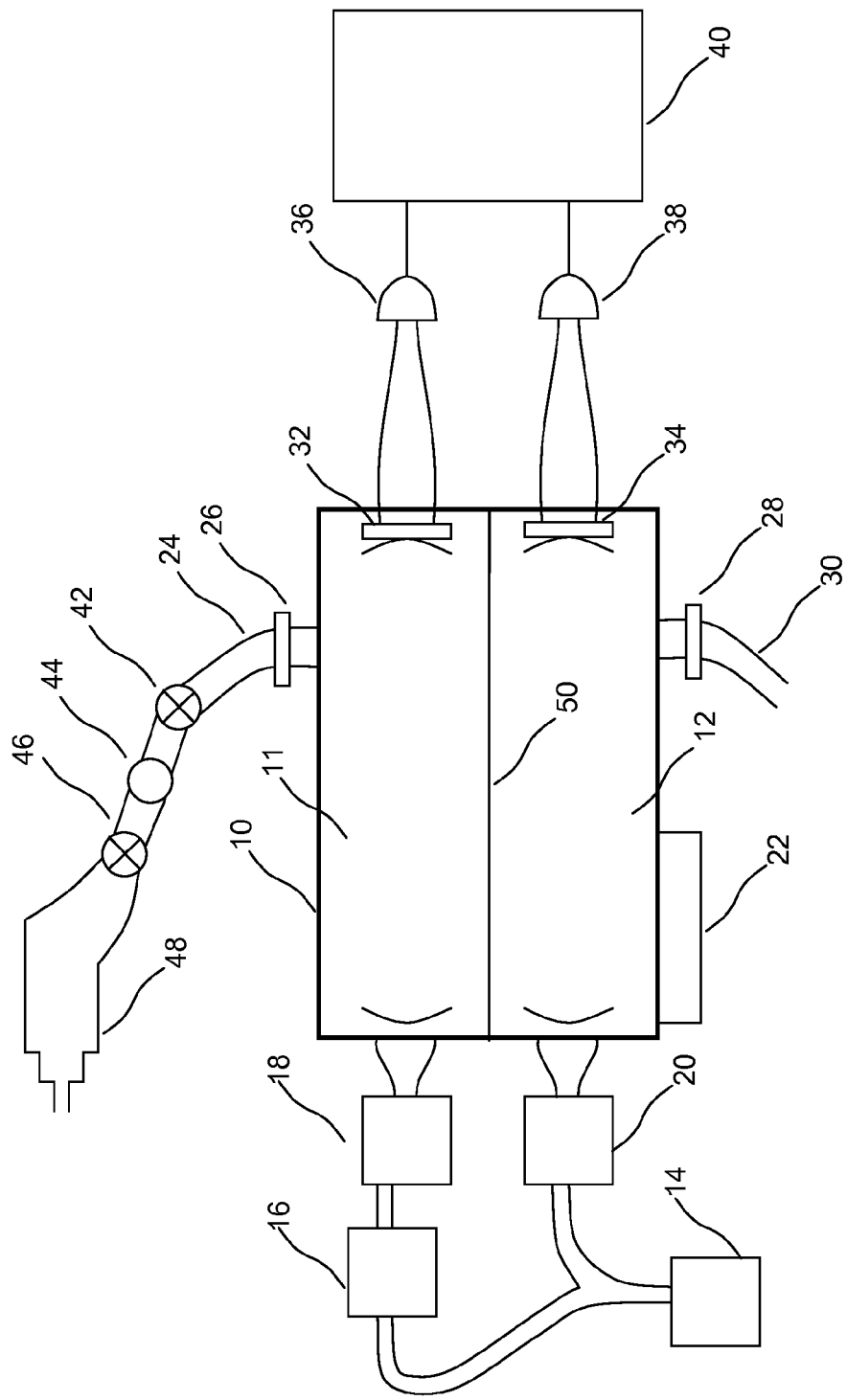
FIG. 1 depicts schematically a dual linear cavity fabricated from a monolithic block for absorption gradiometry.

Two high finesse optical cavities 11 and 12 are constructed from a single, monolithic block 10 as seen in FIG. 1. A material such as Zerodur, with low coefficient of thermal expansion may be used. In addition, active cooling, such as typically done with Peltier coolers (such as 22), can be used to temperature stabilize the entire block at the same temperature. The mirrors are desirably chosen to be highly reflective, low loss mirrors, such as those fabricated on a silica or ultra low expansion glass (ULE) substrate and coated using, for example, ion beam sputtering thin film coating. In addition, cavities can be formed by using micro-cavity structures, such as micro-toroids and photonic band gap resonators.

High finesse mirrors are aligned with one mirror per cavity mounted on a piezo-electric device 32, which allows voltage controlled translation of the mirror. The piezo-electric device can be, for example, a stack actuator or a tube actuator. The two cavity lengths can be precisely adjusted by equating their FSRs. Cavity finesses in excess of about $10^3$, about $10^4$, or about $10^5$ may be employed. The cavities may be evacuated. Although the mirror coatings in the respective cavities may not be identical, and thus the cavity finesses may differ slightly, any finesse difference will cause a constant relative scaling factor and can be characterized. The cold cavity finesses (empty cavity without additional absorbers) can be calibrated by measuring their respective ring down times.

Figure 2:
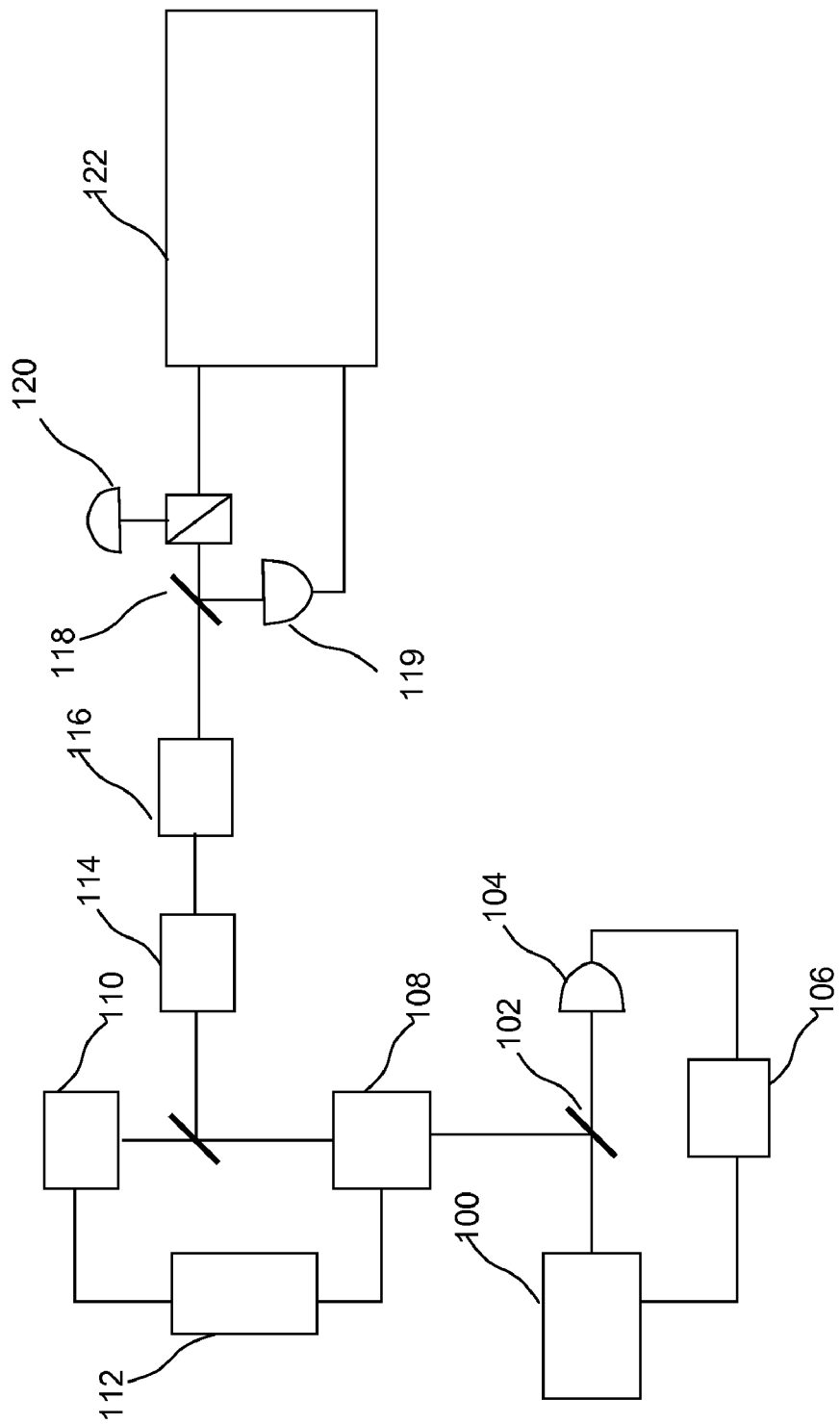
FIG. 2 depicts schematically a cavity trace detection gradiometer.

A single laser 100 is frequency stabilized to a reference 112 such as an atomic or molecular transition line, as shown schematically in FIG. 2. For example, in the visible and near-IR, an alkali or iodine cell can be used as a reference; in the mid-IR, a xenon discharge cell may be used; and in the UV spectrum, an alkaline-earth atom can be used. Alternatively, the laser can be frequency stabilized by locking to an additional high finesse cavity.

In the near-IR, laser 100 may be, for example, a commercially available diode laser (including distributed Bragg reflector (DBR) and distributed feedback (DFB)). Quantum cascade lasers or OPO (optical parametric oscillators) may be used for mid-IR wavelengths.

The laser 100 can be amplitude stabilized with conventional feedback techniques, possibly with feedback to the laser's power supply. For example, a beam splitter 102 diverts a portion of the beam to a photodiode 104 whose output is used by feedback electronics 106 to drive the amplitude of the laser output.

Following the frequency and amplitude stabilization, the laser beam is then propagated through two phase modulators 114 and 116 such as electro-optic modulators or fiber phase modulators, one used to put high frequency sidebands (~GHz) on the light resonant with the FSR of the cavity and the second to put RF sidebands (~100 MHz) used for the cavity stabilization lock. The modulated beam is incident on a beam splitter 118 and coupled into each cavity in the two-cavity module 122 (whose detail is given in FIG. 1). The beam may be fiber coupled and the beam splitter may be a fiber splitter as depicted schematically in FIG. 1.

The optics setup indicated above is designed to minimize the path separation between the two split light beams and minimize the number of separate optics that the beams see.

The cavity resonance, for each cavity 11 and 12, is frequency locked to the master laser locking frequency by separately feeding back to each cavity piezo device 32 and 34 using, for example, a Pound-Drever-Hall locking technique.

This feedback would typically be bandwidth limited to approximately 1 kHz due to mechanical resonances in the piezo and mirror.

Such cavity stabilization to a laser frequency, which is in turn stabilized to an atomic transition line, helps to ensure the long term absolute stability of the cavity modes, as well as the relative stability between the two cavities. Additional high frequency feedback, for example to fiber phase modulators (18 and 20 on FIG. 1), may be implemented in order to maintain coupling of the probe beams into the cavities. Any intensity fluctuations in the master laser beam or noise in the electro-optical modulation (EOM) drivers will however be common mode to both cavity measurements.

For some applications where short time measurements are made under stable conditions, it may be preferable not to have frequency and amplitude stabilization stages for the master laser 100. It may also be preferable to have a piezo in only one of the cavities. In this embodiment, high frequency feedback, such as to the phase modulators, ensures the laser coupling into the cavities. Feedback to the piezo on one cavity stabilizes its length relative to the other.

The intensity of the frequency component used for cavity locking can be made much smaller (for example $10^3$, $10^4$, or $10^5$ times smaller) than the intensity of the probe frequency components, so as to contribute negligibly to the transmitted power detected on the signal photodiodes 36 and 38. For example, the locking beam can be provided by the weak sideband at 100 MHz in the example above, with the carrier off-resonant from any cavity mode (Long 2007). The reflected signal from the locking beam provides the feedback signal for cavity stabilization. A heterodyne detection of the cavity coupled locking sideband with the carrier provides the signal for feedback. A Faraday rotator 16 is placed in the path of one beam in order to separate, with polarization selectivity, the reflected beams from the two cavities and send them to two different photodiodes (119 and 120 in FIG. 2). The photodiodes desirably have large bandwidths (e.g., several GHz) and large responsivity. They desirably would demonstrate low dark current and low NEP (noise equivalent power). These photodiodes may include Si or GaAs based detectors and may also have connectorized preamplifier stages.

In another embodiment, the locking beam may be used as a reference beam for heterodyne detection of the transmitted light. In another embodiment a ring cavity can be used, where the locking beam is incident on one cavity mode in each cavity and the probe beams are separated and then phase modulated and coupled into the counter-propagating cavity modes. In this embodiment back reflection into the master laser can be reduced. Various other mirror configurations, such as bow-tie geometries, can be used to form each optical cavity.

Frequency sidebands used for the probe beam are desirably separated from the cavity locking frequency by an integer number of cavity FSRs. For a 10 cm long cavity, for example, the FSR is 1.5 GHz. Each beam is incident on a separate sensitive photodetector 36 or 38 upon transmission through the cavity. The differential absorption between the two cavities is extracted by a signal processing unit 40. Various embodiments of the signal extraction are delineated below.

In another embodiment of this invention, one or more femtosecond frequency combs (e.g., as described in Thorpe 2008) may be simultaneously referenced to both cavities 11 and 12 in the gradiometer in order to provide multiple simultaneous measurements for increased effective bandwidth.

An external pump is connected to the outside environment in order to sample air and send it through a valved plumbing system which is connected to each cavity, thereby allowing the introduction of gas samples into the cavity. The valves (e.g., 42, 46) can be independently opened remotely by a computer controller. An extension arm such as 48 can be placed at the end of the sampling tube, which can sample ambient air from regions not adjacent to the cavity structure. This may allow some degree of standoff detection, which is desirable, for example, in explosive detection applications. The position of the end of the extension arm may be recorded for each data set. (While FIG. 1 shows valves and an extension arm at the gas inlet of only one cavity, it will be appreciated that they can be used at the gas inlet of all cavities.)

A pressure regulator 44 can be used to stabilize the cavity pressure when the valve is opened. A nested series of valves can be used to pass along the gas sample from the atmosphere to the cavity, with pressure regulation and flow rate controlled at each stage. A buffer gas may be used to fill the cavities. The buffer gas would typically be a relatively non-interacting gas such as $N_2$. Flow of the buffer gas could be connected to one of the valves (42, 46), which could be 3-way valves. Pressure regulation of the buffer gas could be controlled by the pressure regulator 44 and would be connected to a supply of buffer gas.

Filters such as 26 and 28 can be placed on the valves leading to both cavity chambers to filter out most common components found in air such as water vapor. Identical filters can be placed on each cavity to ensure common sampling, which allows gradient sensitivity to the target gas. When both cavities see an air sample, the filter requirements to remove all common atmospheric absorbers are less stringent if atmospheric conditions are more common at both valve locations than are the levels of contaminant.

Alternatively, filters 26 and 28 with different permeability properties can be used. This configuration is useful in applications where expected local gradients of contaminants are negligible and therefore relative concentrations of two different absorbers can be measured. All other noise sources, including those due to the air sampling process, can be reduced due to common mode.

The diffusion of the sampled air through the cavity may occur on timescales not shorter than hundreds of milliseconds, whereas the fluctuations of cavity length may be stabilized with a tight lock feeding back to the piezo actuators 32 and 34 (e.g., with a 1 kHz bandwidth). There may also be a high frequency feedback to the fiber phase modulators 18 and 20. Noise contributions at higher frequencies which may not be common mode can be easily filtered from the signal.

A controller for the trace gas detection gradiometer can control the frequency and intensity of the light sources as well as the feedback signals required for their stabilization. Alternatively the feedback may be carried out by dedicated optical or electronic/optical devices. The controller may also control the operation of the detectors which are used to determine the absorption on the probe beams. The controller may control the power and frequency of the RF sources used for frequency modulation. The controller, generally with the assistance of a signal processing unit, may be expected to record the signal detected on a photodetector and perform the necessary electronic and digital filtering and demodulation in order to extract a sensitive absorption measurement. The controller may control the opening and closing of the air sampling valves as well as the location of the sample extraction by adjusting the pointing and extension of the sampling tubes. The controller will also monitor the pressure regulators and sample insertion flow rate and make required adjustments. The controller desirably has sufficient number of digital and analog channels in order to perform all of these functions. The controller desirably maintains communication, whether wireless or over a standard or custom wired communication system, with other electronic devices. Alternatively, some controller functions may be carried out by software on a primary computer in which case the controller forming part of the physical trace gas detection gradiometer may be very simple.

Cavity Ring Down Gradiometry

In this mode of operation, the master laser is frequency modulated at an integer number of cavity FSRs and these frequency sidebands are used as the probe laser frequencies. The frequency modulated beam is divided on a beam splitter, which can be a 50/50 glass beam splitter or a fiber beam splitter (e.g., 14 in FIG. 1). The beam is switched off and simultaneous ringdown measurements are made in each cavity by detection on two calibrated photodetectors.

In the absence of any absorber, the cavities can be calibrated for their relative ring down times, $$\frac{1}{\tau_1} - \frac{1}{\tau_2} = \delta_1 - \delta_2 \equiv \Delta$$

where for each cavity, $\tau$ and $\delta$ represent the bare cavity ring down times and total cavity loss scaled by cavity length. Although the individual $\delta$ may fluctuate over time due to temperature, acoustic vibrations, or other technical noise sources, their difference $\Delta$ is expected to remain essentially constant over time due to the common mode nature of the fabrication of the device. After this calibration, a measurement may be carried out. The two ring down times $\tau'_1$ and $\tau'_2$ are measured after inserting samples into the cavities via ambient air sampling. The difference $$\left(\frac{1}{\tau'_1} - \frac{1}{\tau_1}\right) - \left(\frac{1}{\tau'_2} - \frac{1}{\tau_2}\right) = \left(\frac{1}{\tau'_1} - \frac{1}{\tau'_2}\right) - \left(\frac{1}{\tau_1} - \frac{1}{\tau_2}\right) = c(\alpha_1 - \alpha_2)$$

provides the relative absorption.

In this embodiment, the ring down time measurement is insensitive to intensity fluctuations, and fluctuations in cavity loss are common mode to both cavities. Therefore this process is less susceptible to empty cavity changes occurring between the time of the cavity calibration and the absorption measurement than are ring down measurements performed with a single cavity. This double cavity technique can also be applied to AC heterodyne ring down techniques (described, e.g., in Ye and Hall 2000).

Continuous Intensity Measurement

In this embodiment the master light is frequency modulated as above. Each probe incident on each cavity is composed of multiple frequency components separated by an integer number of cavity FSRs. The transmitted light is measured on two photodiodes, where the signal at each photodiode is demodulated at the frequency corresponding to the frequency difference between the two sidebands on the probe for each cavity or the frequency difference between a sideband and the carrier frequency. This high frequency demodulation renders this FM technique insensitive to low frequency photodetector noise.

The empty cavity transmitted intensity is calibrated. The ratio $\chi$ of the transmitted intensities in the absence of an absorber is nominally constant due to common mode construction and common cavity stabilization.

Unlike in a single cavity measurement, the relative constant empty cavity transmission allows this continuous measurement to have reduced sensitivity to intensity fluctuations, while still benefiting from AC detection. The ratio of the two demodulated signals from the two cavities is $$\frac{I_1}{I_2} = \chi e^{-(\alpha_1 - \alpha_2)} \approx \chi(1 - [\alpha_1 - \alpha_2])$$

which allows a continuous noise insensitive measurement of the difference in absorption between the two cavities.

Background Subtraction

Either of the two detection techniques with multiple cavities illustrated above can be used for absolute trace gas detection by introducing a sample gas in only one of the cavities. In this embodiment the second cavity is being used as a reference for both the initial cavity calibrations and the absorption measurement.

Gradient Measurement

In this embodiment a sample is introduced into each cavity, by sampling regions of the air that are spatially separated by the distance between the intake tubing for each cavity. This separation difference is not constrained to be equal to the physical separation of the cavities, but can be arbitrarily optimized for a specific application corresponding to the expected spatial separation scale of the gradient. For example, this separation may be determined by the expected size of a landmine.

In addition, multiple gradient measurements may be taken without moving the cavities, and without changing the separation of the cavities, by sampling from different regions. These measurements can be used to locate the source of the vapor emissions, for example, a landmine or the initial emission point of a diffusing chemical weapon. Subsequent measurement locations can be determined based on real time analysis of measurements at prior locations. In this embodiment the tubing is preferably on a movable extraction device. The controller can extend the extraction arm and rotate it to sample air from the desired location. The controller may also store complete information relating extraction locations to relative absorptive measurements. The extension tubes can have a GPS sensor which can record the exact location of the sample extraction.

Gradients in a background gas can be distinguished from gradients in the signal contaminant due to different length scales and time evolution by varying time and space parameters in a sequence of measurements.

Plume Direction Flow

In this embodiment, simultaneous measurements are made in both cavities using either of the techniques above. A series of measurements are made separated by a chosen time interval and the change in relative absorption between the cavities over time can be extracted. The flow direction and flow rate of the absorbing vapor can be determined from this sequence.

Absorption Measurements with Gain Element or Saturable Absorber

Absorption measurements under some conditions can be made more sensitive by inserting a gain element or saturable absorber in the cavity along with the trace gas sample to be measured. For example, the gain medium can be a helium-neon gas cell, a semiconductor diode laser with AR coating on both facets or an atomic vapor cell under lasing without inversion conditions. A saturable absorber could be, for example, an atomic vapor cell.

Technical complications of such an apparatus include stabilizing the gain element or saturation condition. By operating in gradiometer configuration as disclosed in this invention, noise from the gain or saturation element such as due to density fluctuations in the medium can be rendered common mode, providing reduced measurement sensitivity to this noise.

Cavity Array for Gas Selectivity based on Diffusion Constants

In this embodiment, an array of two or more optical cavities are assembled from a monolithic block as above, all stabilized to a common atomic frequency reference. However, there is no physical barrier between the cavity volumes in this embodiment (so that the divider 50 of FIG. 1 is not present). A gas is introduced into the sensor (either through a breathing tube or a sampling tube as in previous embodiments), but only on one side, and it then diffuses across the volume enclosed by the two cavities. The diffusion of the gas in the direction perpendicular to the cavity axis is detected.

The laser frequency used in this embodiment would be chosen to maximize the relevant absorption cross section of anticipated trace particles. For example, for volatile organic compound (VOC) detection, lasers operating in the mid-IR would be desirable. For breathalyzer applications NIR to mid-IR wavelengths can be used.

Molecules have diffusion constants in a gas which scale inversely with the square root of their mass; therefore, by monitoring the diffusion of a gas sample, one can in principle identify the components by determining their diffusion rates. The intensity transmission profiles measured at each cavity output collectively provide a sensitive recording of the time of flight of a gas mixture. The profiles can be analyzed to extract the absorption contributions from gases with differing characteristic diffusion times. A Bayesian estimation algorithm provides optimum signal analysis and corresponding trace gas detection and identification.

Figure 3:
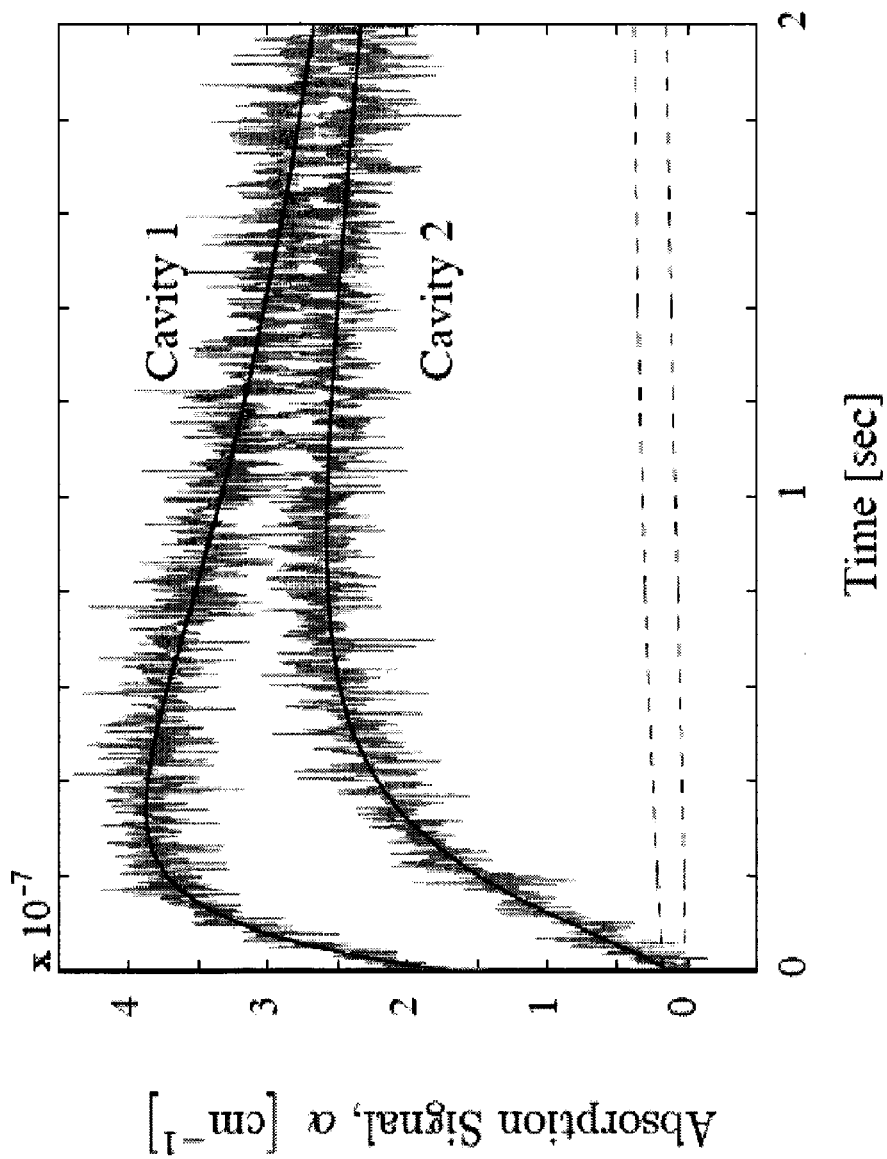
FIG. 3 depicts simulated traces of the absorption of light through two cavities in the presence of ethane diffusion. Dashed lines show an initial guess for traces based on lack of information of known species or concentration, and solid lines show fits.

As an illustration of this estimation process, we consider a sample of ethane ($C_2H_6$) which diffuses across two cavities (e.g., 11 and 12 in FIG. 1, modified so that divider 50 is not present), which comprise the linear array. We have assumed that each cavity has an absorption sensitivity of $10^{-9}$/cm/sqrt (Hz), as represented by the noise in the simulation. FIG. 3 shows the simulated intensity transmission traces taken at each cavity, as well as our initial guesses (dashed lines), which convey that initially we essentially do not know the concentration or identity of the VOC. The final fits (solid lines) converge to a measurement error of less than 1% in both concentration and diffusion constant. For these parameters, the analyte particle number as well as its identification is reliably expected at 1 ppb (part-per-billion) concentration.

This embodiment has additional applications in volatile organic compound detection such as for environmental monitoring and for medical diagnostic breathalyzers. The human breath has thousands of markers which can be used for diagnostics as well as early detection for kidney disease and cancer. Breathalyzers, which analyze these markers when a patient breathes into a tube, require both good sensitivity and selectivity as provided by this cavity array technology.

In another embodiment, a gradiometer can be fabricated with cavity arrays as above on both sides of a divider. In this case the diffusion detection would take place independently in both cavity arrays within the monolithic block. Thus gas would be introduced into both chambers, where each chamber consisted on multiple cavities linearly arranged in an array and diffusion constants can be extracted from each array measurement.

REFERENCES

"Application of Mid-Infrared cavity ring down spectroscopy to trace explosives vapor detection," M. W. Todd et al., Applied Physics B 75, 367-376 (2002).

"Ultrasensitive detections in atomic and molecular physics" J. Ye, L. Ma and J. Hall, J. Opt. Soc. Am. B 15, 6-15 (1998).

"Cavity enhanced optical frequency comb spectroscopy: application to human breath analysis," M. Thorpe et al., Op. Exp. 16, 2387-2397 (2008).

"Cavity ringdown heterodyne spectroscopy: high sensitivity with microwatt light power," J. Ye and J. Hall, Phys. Rev. A 61, 061802-061805 (2000).

"Multiple frequency modulation for low light measurements in an optical cavity," R. Long, A. Tuchman and M. Kasevich, Opt. Lett. 32, 2502-4 (2007).

"Ringdown cavity spectroscopy cell using continuous wave excitation for trace species detection," K. Lehmann, U.S. Pat. No. 5,528,040 (1996).

"Cavity ringdown spectroscopy system using differential heterodyne detection," J. Ye and J. Hall, U.S. Pat. No. 6,727,492 (2004).

"Cavity locked ringdown spectroscopy," R. Zare et al., U.S. Pat. No. 6,084,682 (2000).

STANDARD MATERIAL AT THE END OF THE APPLICATION

It is to be understood that while the invention has been described in conjunction with preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

We claim:

1. A trace gas detector comprising:
   (a) two or more high finesse optical cavities for receiving one or more gaseous samples for detection,
   (b) a laser,
   (c) a frequency reference for the laser,
   (d) an optical subsystem that
      (d1) splits a laser beam of light emitted by the laser into two or more split laser beam portions, and
      (d2) directs one of the two or more split laser beam portions through each of the two or more high finesse optical cavities,
   (e) two or more photodetectors, wherein each of the two or more photodetectors monitors the split laser beam portion directed through one of the two or more high finesse optical cavities by the optical subsystem,
   (f) a sampling mechanism that obtains one or more gaseous samples for detection and propagates the one or more gaseous samples through the two or more high finesse optical cavities, and
   (g) a controller that:
      (g1) controls intensity and frequency content of light emitted by the laser,
      (g2) receives information from the two or more photodetectors, (g3) determines a relative absorption between the two or more high finesse optical cavities based upon the information received from the two or more photodetectors, and (g4) directs the operation of the sampling mechanism.

2. The trace gas detector of claim 1, wherein the two or more high finesse optical cavities are constructed from a monolithic structure.

3. The trace gas detector of claim 1, wherein the frequency reference is an atomic vapor cell.

4. The trace gas detector of claim 1, wherein the frequency reference is a high finesse optical cavity.

5. The trace gas detector of claim 1, wherein the sampling mechanism can sample from a range of locations.

6. The trace gas detector of claim 1, wherein the sampling mechanism comprises filters to filter out components of the one or more gaseous samples.

7. The trace gas detector of claim 1, wherein the sampling mechanism obtains samples of air from the atmosphere.

8. The trace gas detector of claim 1, wherein the sampling mechanism obtains samples of air from human breath.

9. The trace gas detector of claim 1, further comprising a Faraday rotator in the path of the laser beam.

10. The trace gas detector of claim 1, wherein at least one cavity comprises a piezoelectric component which can adjust the cavity length.

11. The trace gas detector of claim 1, further comprising equipment for heterodyne detection of the beam intensity at the output of at least one cavity.

12. The trace gas detector of claim 1, wherein each cavity has a gas inlet, and at least one gas inlet comprises a valve.

13. The trace gas detector of claim 12, wherein at least one gas inlet comprises a pressure regulator.

14. The trace gas detector of claim 12, wherein at least one gas inlet comprises an extension arm.

15. The trace gas detector of claim 1, further comprising a mechanism for the introduction of a buffer gas.

16. The trace gas detector of claim 1, wherein at least one of the two or more high finesse optical cavities comprises an intracavity gain medium or saturable absorber.

17. A trace gas detector comprising:
a first high finesse optical cavity;
a second high finesse optical cavity, wherein the second high finesse optical cavity is separated from the first high finesse optical cavity by a divider;
a laser;
a frequency reference for the laser;
an optical subsystem that splits a laser beam of light emitted by the laser into at least a first split laser beam portion and a second split laser beam portion, said optical subsystem directing the first split laser beam portion through the first high finesse optical cavity and directing the second split laser beam portion through the second high finesse optical cavity;
a first photodetector that monitors the first split laser beam portion directed through the first high finesse optical cavity;
a second photodetector that monitors the second split laser beam portion directed through the second high finesse optical cavity;
a sampling mechanism that introduces one or more gaseous samples for detection into the first high finesse optical cavity and one or more gaseous samples for detection into the second high finesse optical cavity; and
a controller that
controls intensity and frequency content of the laser beam of light emitted by the laser,
receives information from the first photodetector and the second photodetector,
determines a relative absorption between the first high finesse optical cavity and the second high finesse optical cavity based on the information received from the first photodetector and the second photodetector, and
directs operations of the sampling mechanism.

18. A trace gas detector comprising:
a first high finesse optical cavity;
a second high finesse optical cavity;
a laser;
a frequency reference for the laser;
an optical subsystem that splits a laser beam of light emitted by the laser into at least a first split laser beam portion and a second split laser beam portion, said optical subsystem directing the first split laser beam portion through the first high finesse optical cavity and directing the second split laser beam portion through the second high finesse optical cavity;
a first photodetector that monitors the first split laser beam portion directed through the first high finesse optical cavity;
a second photodetector that monitors the second split laser beam portion directed through the second high finesse optical cavity;
a sampling mechanism that introduces one or more gaseous samples for detection into the first high finesse optical cavity, there being no physical barrier between the first high finesse optical cavity and the second high finesse optical cavity thus allowing the one or more gaseous samples introduced into the first high finesse optical cavity to diffuse into the second high finesse optical cavity; and a controller that controls intensity and frequency content of the laser beam of light emitted by the laser, receives information from the first photodetector and the second photodetector,
determines a relative absorption between the first high finesse optical cavity and the second high finesse optical cavity based on the information received from the first photodetector and the second photodetector, and
directs operations of the sampling mechanism.

\* \* \* \* \*